United States Patent [19]

Venturello et al.

[11] Patent Number: 5,274,140

[45] Date of Patent: Dec. 28, 1993

[54] PROCESS FOR CATALYTICALLY EPOXIDIZING OLEFIN WITH HYDROGEN PEROXIDE

[75] Inventors: Carlo Venturello, Torino; Enzo Alneri; Giulio Lana, both of Novara, all of Italy

[73] Assignee: Instituto Guido Donegani, S.p.A., Italy

[21] Appl. No.: 582,814

[22] Filed: Sep. 14, 1990

Related U.S. Application Data

[63] Continuation of Ser. No. 449,316, Dec. 11, 1989, abandoned, which is a continuation of Ser. No. 54,036, May 22, 1987, abandoned, which is a continuation of Ser. No. 696,707, Jan. 31, 1985, abandoned, which is a continuation of Ser. No. 290,092, Aug. 4, 1981, abandoned, which is a continuation of Ser. No. 170,157, Jul. 18, 1980, abandoned.

[30] Foreign Application Priority Data

Jul. 19, 1979 [IT] Italy .............................. 24478 A/79
Mar. 7, 1980 [IT] Italy .............................. 20418 A/80

[51] Int. Cl.⁵ .......................................... C07D 301/12
[52] U.S. Cl. ..................................................... 549/531
[58] Field of Search ........................................... 549/531

[56] References Cited

U.S. PATENT DOCUMENTS

| | | | |
|---|---|---|---|
| 2,833,787 | 5/1978 | Carlson et al. | 549/531 |
| 2,833,788 | 5/1958 | Skinner et al. | 549/531 |
| 2,992,237 | 7/1961 | Dieckelmann et al. | 549/531 |
| 3,992,432 | 11/1976 | Napier et al. | 260/465.1 |
| 3,998,856 | 12/1976 | Rosenberger | 549/519 |
| 4,286,068 | 8/1981 | Mares et al. | 549/531 |

FOREIGN PATENT DOCUMENTS

| | | |
|---|---|---|
| 860776 | 5/1978 | Belgium . |
| 633384 | 12/1961 | Canada .............................. 549/531 |
| 2347224 | 4/1974 | Fed. Rep. of Germany . |
| 2300765 | 9/1976 | France . |
| 137913 | 12/1978 | Japan .............................. 549/531 |
| 1423028 | 1/1976 | United Kingdom . |
| 1491635 | 11/1977 | United Kingdom . |

OTHER PUBLICATIONS

J. M. McIntosh, "Phase-Transfer Catalysis using Quaternary Onium Salts", Journal of Chemical Education, vol. 55(4), Apr. 1978, pp. 235-238.

M. Pralus et al, Fundamental Research in Homogeneous Catalysis, vol. 3, (1979), pp. 327-343.

Richard P. Heggs et al, Jour. Am. Chem. Soc., vol. 101(9), Apr. 25, 1979, pp. 2484-2486.

C. Venturello et al, J. Org. Chem., vol. 48 (1983) pp. 3831-3833.

H. Mimoun et al, Tetrahedron, vol. 26 (1970), pp. 37-50.

D. Swern, editor, "Organic Peroxides", vol. II (1971), pp. 452-453.

R. D. Bach et al, J. Org. Chem., vol. 44(14) (1979), pp. 2569-2571.

Stark, Tetrahedron Letters, vol. 22(22) (1981) pp. 2089-2092.

Carlo Venturello et al, Journal of Molecular Catalysis, vol. 32 (1985), pp. 107-119.

*Primary Examiner*—C. Warren Ivy
*Assistant Examiner*—Ba K. Trinh
*Attorney, Agent, or Firm*—Morgan & Finnegan

[57] ABSTRACT

There is disclosed a new process for the epoxidization of olefins by reaction with hydrogen peroxide according to the double phase technique with "onium" salts, characterized in that the reaction is conducted in a liquid aqueous-organic biphasic system consisting of:

(a) an organic phase substantially containing the olefin, and (b) an aqueous acid phase substantially containing hydrogen peroxide, in the presence of a catalytic system consisting of a first component which is at least one element selected from W. Mo, V or at least one derivative of said elements, and of a second component which is at least one derivative selected from the derivatives of P and As.

26 Claims, No Drawings

PROCESS FOR CATALYTICALLY EPOXIDIZING OLEFIN WITH HYDROGEN PEROXIDE

This is a continuation of co-pending application Ser. No. 449,316, filed on Dec. 11, 1989, now abandoned, which is a continuation of application Ser. No. 054,036, filed May 22, 1987, now abandoned, which is a continuation application of Ser. No. 696,707, filed Jan. 31, 1985, now abandoned, which is a continuation application of Ser. No. 290,092, filed Aug. 4, 1981, now abandoned, which is a continuation application of Ser. No. 170,157, filed Jul. 18, 1980, now abandoned.

BACKGROUND OF THE INVENTION

Quite a number of processes directed to the epoxidization of olefins are known, although the greatest part of them are methods which either did not find a practical industrial application or are now of no interest because not possessing, to a sufficient extent, all of the requisites of an applicable and economical character and, lately, also of ecological acceptability, etc., necessary for rendering them entirely acceptable for industrial use.

Even at the present time, besides the direct oxidation of ethylene to ethylene oxide, the propylene oxide, and at any rate the epoxides in general, are obtained almost exclusively by the known chlorohydrin process.

Schematically, that process consists in reacting an olefin with chlorine water obtaining thereby the chlorohydrin which is treated successively with alkalis (lime) thereby obtaining the corresponding epoxide. However, the process is subject to ever-increasing difficulties from the industrial point of view as well as on the economical plane, and with respect to environmental compatibility. In fact, the chlorohydrin process leads to the contemporaneous, more or less abundant and difficult to control, production of both mineral as well as organic chlorinated by-products which, while not useful, present major problems in the qualitative and quantitative disposal thereof.

To this must be added the growing cost of the chlorine, strictly bound to energy consumption, and other factors.

Therefore, quite recently interest was aroused in the epoxidization of an olefin by a process conducted in anhydrous organic phase with an organic hydroperoxide and in the presence of catalysts based on molybdenum, tungsten or vanadium, of which there have been some actual industrial applications.

However, that process has the disadvantage that production of the epoxide is accompanied by the production of the alcohol corresponding to the hydroperoxide, in quantities equivalent to or even greater than the epoxide. Exploitation of the alcohol as such, or recycle thereof, represents serious economical burdens which substantially affect commercial use of this process.

Research has been directed, also, to more direct oxidation methods.

Thus, epoxidization processes by means of molecular oxygen with silver catalysts, etc., have been proposed. Those processes had only limited success in the case of ethylene. The techniques proved to be not extendible to other olefins of significant interest, e.g., propylene.

Hydrogen peroxide, due to its oxidizing action associated with the absence of environmental problems, problems of pollution, etc., has been suggested as suitable for a certain number of epoxidization processes.

According to those processes, since the activity of the hydrogen peroxide toward the olefins as such is rather limited or altogether absent, it is necessary to use activating agents, in general organic acids such as for instance formic acid, acetic acid, etc., in organic solvents, which acids, in the form of peracids, form "in situ" the reactive epoxidizing agent.

Those processes, also, do not seem to have achieved any real success, both because of the difficulty of obtaining peracids as well as because of the instability of the epoxides in an acid medium which makes necessary rather burdensome operating conditions.

Other processes have been described as applicable selectively to the preparation of epoxy-alcohols (glycydols) by an epoxidization of hydrosoluble olefins with hydrogen peroxide, in an aqueous solution containing primary or secondary alcohols, and in the presence of catalysts based on: Mo, V, W.

In this last-mentioned case, it is a question of a technique substantially directed towards glycydols only, compounds that are of a limited commercial interest. On the other hand, the opoxidization reaction of the olefins with hydrogen peroxide leads to the formation of water which, especially when metal catalysts are used in the form of peroxides inhibits, with its accumulations, the reaction itself, a drawback which it was attempted to obviate by the use of concentrated solutions of hydrogen peroxide, as well as by using potentiated catalytic systems.

Thus, there have been described olefins oxidizable by reaction with highly concentrated hydrogen peroxide in a homogeneous, essentially organic liquid phase, in the presence of catalytic systems soluble in the organic liquid and based on elements of the IV, V and VI B (Ti, V, Mo, W) groups, of the Periodic Classification of Elements associated with elements selected from Pb, Sn, As, Sb, Bi, Hg, and so on.

The results did not meet expectations on the practical level because of the slowness of the reaction and of the expensiveness of the catalytic system consisting, in general, of very sophisticated organometallic compounds, necessary for their solubility in the organic medium.

Moreover, the use of hydrogen peroxide of high concentration (>70%) involves some risks from the point of view of safety, not easily economically surmountable.

Improvements have been described as achievable by the use, in the above-mentioned technique, of catalysts based on tungsten or molybdenum or of arsenic or boron with an excess of olefin, in general, in combination with continuous distillation of the interfering water.

Here, also, the use of concentrated solutions (>70%) of hydrogen peroxide is practically required, with the corresponding handling problems connected with it as already mentioned with regard to the safety of the installations. Moreover, the continuous removal of the reaction water besides that introduced by the hydrogen peroxide itself, an operation that makes the high $H_2O_2$ concentrations practically necessary from the start, proves particularly economically burdensome.

On the other hand, the oxidization of the olefins with hydrogen peroxide involves an intrinsic contradiction resulting from the operating conditions which require at best an aqueous medium, possibly acid, as far as the catalytic system and the hydrogen peroxide are concerned, while the oxidization reaction and the stability of the epoxide require preferably a neutral organic medium.

All of the prior processes discussed above, and which involve the use of hydrogen peroxide, substantially tend to make the reaction medium homogeneous in some way and also tend to avoid the inhibiting accumulation of $H_2O$, with rather uncertain results, at least from the point of view of the actual industrial feasibility of such processes.

It is known from the literature to conduct chemical reactions in general substantially based on the ionic exchange, according to the so-called "double phase" technique.

There has also been described the possibility of epoxidizing olefins with hydrogen peroxide, in a double phase, in the presence of mineral derivatives based on tungsten and molybdenum. We are not aware of any practical interest in the method because of the poor efficiency of the catalyst, also verified by us, and therefore the double-phase technique has not appeared to be at all convenient or commercially feasible.

THE PRESENT INVENTION

One object of this invention is to provide a process for the catalytic epoxidization of olefins, using hydrogen peroxide, as an oxidizing agent, which process is relatively simple, economical, and free of the drawbacks of the processes known heretofore.

A particular object of this invention is to provide a process for the catalytic epoxidization of olefins with diluted hydrogen peroxide, characterized in having a high degree of selectivity for the desired epoxide which is obtained means of an efficient long-life catalytic system, without requiring a burdensome continuous distillation of the reaction water.

In the process of this invention, the contradiction inherent in the usual operating conditions is effectively overcome by the use of the reaction technique conducted in a double, aqueous-organic liquid phase.

Said technique involves the use of two unmixable or hardly mixable reaction means of differing polarity, so that both the pH control, as well as the concentration of the hydrogen peroxide and the elimination of the reaction water, are substantially less constrictive of the practical effectiveness of the process.

We have found that the epoxidization reaction of olefins with hydrogen peroxide catalyzed by compounds based on transition metals, can be made both convenient and practical by the use of a particular catalytic system which, unexpectedly exhalting the epoxidization reaction, permits of conducting the the epoxidization reaction of the olefins in an economical, handoperational and easy way, according to the "doublephase" technique.

Summing up, the present invention represents the surprising overcoming of a prejudice existing in the prior art, according to which the epoxidization reaction of olefins with hydrogen peroxide, in the presence of catalysts, and conducted according to the double-phase technique would not lead to practical results. This situation appears to have deterred the skilled in the art from further research in the field and from expecting the surprisingly better results obtained by the process.

These and other objects which will be apparent to those skilled in the art from the following description, are achieved, according to this invention, by reacting the olefins to be epoxidized with hydrogen peroxide according to the "double phase" technique with "onium" salts, characterized in reaction is conducted in a double-phase aqueous-organic liquid system consisting of:

(a) an organic phase substantially containing the olefin; and
(b) an aqueous acidic phase substantially containing hydrogen peroxide;

in the presence of a catalytic system consisting of at least one element selected from W, Mo, V or of at least one derivative of said elements, and of at least one derivative selected from those derived from P and As.

The reaction may be represented by the following scheme:

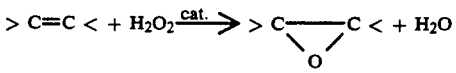

The reaction is conducted in the double-phase, aqueous-organic system, under vigorous stirring, in the presence of the above-defined catalytic system. The organic phase consists of the olefin and possibly of an organic solvent and the aqueous phase of the hydrogen peroxide.

The temperature and the operating pressure are practically determined by the reactivity and by the nature of the olefin, by the stability of the hydrogen peroxide and of the "onium" salts used in the organic medium.

Temperatures comprised between 0° C. and 120° C. and pressures between atmospheric pressure and about 100 atmospheres are, in general, sufficient.

The olefins subjected to the epoxidization reaction have the following formula:

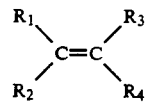

wherein $R_1$, $R_2$, $R_3$ and $R_4$, which can be substituted with functional groups inert under the reaction conditions, represent hydrogen atoms or hydrocarbylic groups such as the alkyls and alkenyls, having up to 30 carbon atoms, cycloalkyls and cycloalkenyls with from 3 to 12 carbon atoms, and which can be branched, aryls, alkyl-aryls, alkenyl-aryls having from 6 to 12 carbon atoms; moreover, a $R_1$, $R_2$, $R_3$, $R_4$ group taken together with an adjacent group may represent alkyl or alkenyl groups having from 1 to 12 carbon atoms in the resulting cycle.

Substituent groups, inert under the reaction conditions, are, for instance: hydroxyl groups, halogens (Cl, Br, F, I), nitro-, alkoxyl, amine, carbonyl, carboxyl, ester, amide, or nitrile groups, and the like.

The $R_1$, $R_2$, $R_3$ and $R_4$ groups may also be alkenyls, in other words, the process according to this invention is applicable also to polyolefins such as dienes, trienes, conjugated or not.

Olefins suited for the epoxydization according to this invention include, by way of examples: alkylic, alicyclic, alkylarylic unsaturated hydrocarbons such as: propylene, butenes, pentenes, and in general the linear or branched mono-and di-olefins having up to 20 carbon atoms, cyclohexene, norbornene, limonene, camphene, vinyl-cyclohexene, styrene, indene, stilbene, etc., unsaturated alkyl halides such as: allyl halides; unsaturated acids and their esters such as: acrylic, methacrylic, crotonic, oleic acid, etc.; unsaturated alcohols and their esters, such as: allyl alcohol, etc.; unsaturated aldehydes and ketones such as: methylallyl acetone, etc.

Definitely acid pH values increase the stability of the hydrogen -peroxide, but make the epoxide unstable. Thus, convenient pH values are those comprised between about 2 and 6. Said range of pH values is obtained in practice directly by the presence of the system consisting of the reactants and of the catalyst used, or, if necessary, the pH may be adjusted by means of mineral acids (HCl, etc.).

On the other hand, as already indicated herein, the double-phase reaction technique renders the operation of the process less sensitive to occasional variations in the pH value.

The duration of the reaction depends on the nature and on the quantity of the catalyst, on the solvent medium and on the olefin used in the process. In general, times comprised between just a few minutes and several hours will be sufficient for completing the reaction.

The quaternary "onium" salts used in the process are known salts that are comprised in the formula:

$$(R'_1, R'_2, R'_3, R'_4M)^+ X^-,$$

wherein M is a pentavalent element belonging to Group V A of the Mendelyeev Periodic System; $X^-$ is a stable anion such as: Cl, Br, $HSO_4^-$, $NO_3^-$, etc., $R'_1$, $R'_2$, $R'_3$ and $R'_4$ represent monovalent hydrocarbyl groups having a total number of carbon atoms of up to 70, but preferably comprised between 25 and 40.

Depending on whether M is an atom of N, P, As or Sb, one obtains the corresponding "onium" salt, i.e., the ammonium (N), phosphonium (P), arsonium (As) or stibonium (Sb) salt.

The catalytic system comprises, according to the invention, a first component consisting of at least one element or of at least one of its minerals, organic or organometallic derivatives selected from W, Mo, V, but preferably W, capable of being transformed, "in situ" and under the reaction conditions, into a compound which is catalytically active.

Derivatives of such elements, having such characteristics, are the oxides, mixed oxides or salt oxides, the oxyacids, the homopolyacids, and their salts, the heteropolyacids, (e.g., silico-molybdic acid, silicon-tungstenic acid etc.), and their salts; the salts derived from mineral hydrogen-acids (e.g., HCl, etc.), the naphthenates, the acetyl-acetonates, the carbonyl derivatives, etc.

First components of the catalytic system which are particularly effective are, besides the elements W, Mo and V as such, the tungstenic, molybdic, vanadic acids and the corresponding neutral salts or acid salts of alkaline and alkaline earth metals, the metal-carbonyls $W(CO)_6$, $Mo(CO)_6$; the $MoO_2$, $Mo_2O_5$, $Mo_2O_3$, $MoO_3$, $WO_2$, $WO_2O_5$, $WO_3$, $VO_2$, $V_2O_3$, $V_2O_5$ oxides; the $WS_2$, $WS_3$, etc., sulphides and the oxychlorides, chlorides, naphthenates and stearates of molybdenum, tungsten, vanadium, etc.

The second component of the catalytic system, according to the invention, consists of at least one mineral, organic or organometallic derivative of an element selected from phosphorus and arsenic, capable of forming with the first component, under the reaction conditions, a catalytically active system.

Derivatives having such characteristics are: the oxides, oxyacids and their salts; the sulphides, the salts derived from hydrogen acids (HCl, etc.), the compounds of formula: $R''_1 R''_2 M(=O)X$, $R''_3 M(=O)XY$, wherein M is an element as defined above, $R''_1$, $R''_2$ and $R''_3$ represent hydrogen atoms, alkyl groups, cycloalkyl groups, aryl or alkyl-aryl groups having up to 12 carbon atoms and where X and Y represent hydrogen, hydrocarbyls (alkyls, aryls, etc.), halogens (chlorine), hydroxy, alkoxy, carboxy groups, mineral oxyacids, etc.

Particularly effective second components of the catalytic system are phosphoric, phosphorous, polyphosphoric, pyrophosphoric, arsenious, arsenic, phosphonic or arsonic acids and their alkaline salts, the oxides $P_2O_3$, $P_2O_5$, $As_2O_3$, $As_2O_5$; the oxychlorides or fluorides and the phosphorous and arsenic chlorides.

The two or more element components of the catalytic system used in this process may belong to different molecules or they may be part of the same complexed molecule comprising the two or more element components.

In that case, there may be used heteropolyacids known as: phosphotungstic, arsenotungstic, phosphomolybdic, heteropolyacids, etc., or their alkaline or alkaline earth salts.

They may easily be obtained by heating and acidifying a solution consisting, for instance, of a tungstate, and of a salt of the central atom of the complex in the appropriate state of oxidization, according to known methods.

Analogously, the compounds of formula:

$$R''_1 R''_2 M(=O)X \text{ and } R''_3 M(=O)XY$$

as defined above, are either available on the market or may be prepared by means of known or conventional techniques.

The two or more components of the catalytic system are used according to a mutual atomic ratio, expressed as the total of the metals belonging to the first with respect to the total of those belonging to the second group of the above-defined elements, and comprised between 12 and 0.1, but preferably between about 1.5 and 0.25.

The catalytic system is used in quantities comprised between 0.0001 and 1 g-atom of metal or of total metals belonging to the first group of elements per 1 mol of hydrogen peroxide, but preferably comprised between 0.005 and 0.2 g-atom per about 1 mole.

Mixtures of the elements and/or their derivatives may also be used to obtain the catalytic system.

The quantity of quaternary or "onium" salt present in the heterogeneous system, may vary within wide limits. Effective results can be achieved by using from about 0.01 mol to 2 mols of "onium" salt per 1 g atom of catalyst, but preferably from 0.1 mol to 1 mol per 1 g-atom, referred to the first component or to the sum of the first components.

Effective "onium" salts include dicetyldimethylammonium chloride, tricaprylmethylammonium chloride, hexadecyltributylphosphonium chloride and the like.

The reactants are used in substantially equimolecular ratios, and a limited excess or lack of the one in respect of the other of the reactants is not detrimental to the course of the reaction.

Illustratively, workable operating values may be considered ratios comprised between 0.1 mol and about 50 mols of olefin per mol of hydrogen peroxide, but preferably values comprised between about 1 mol and 20 mols.

The reaction is conducted, as previously indicated, according to the double-phase technique. More particularly, the organic phase (a) may indifferently consist of the reacting olefin itself, used in a suitable excess, or it may consist of the reacting olefin dissolved in appropriate extraneous organic solvents.

As solvents for the organic phase there are used inert solvents substantially unmixable with the aqueous phase; effective practical results are obtained by the use of aliphatic, alicyclic or aromatic hydrocarbons such as: heptane, octane, cyclohexane, benzene, toluene, xylenes, etc., chlorinated hydrocarbons such as: dichloromethane, trichloromethane, chloroethane, chloropropane, dichloroethanes, trichloroethanes, tetrachloroethanes, di- and trichloropropanes, tetrachloropropanes, chlorobenzene, or by the use of alkyl esters such as: ethyl acetate or suitable mixtures comprising the same.

The skilled in the art can choose the type of organic phase (a) depending, for instance, on the reactivity of the starting olefin and on the parameters used in each instance. When inert solvents as listed above are used as solvents for the organic phase, the concentration of the olefin in the solvent is not critical to the performance of the process.

Operating values for the olefin concentration in the organic phase are comprised between 5% and about 95% by weight; higher values or lower values are however compatible within the limits of their practicability. The concentration of hydrogen peroxide in the aqueous phase may be maintained between 0.1 and about 70% by weight.

However, the process of this invention has the advantage of permitting use of low hydrogen peroxide concentrations. Hydrogen peroxide concentrations comprised between 1% and about 10% have proved to be effective. Concentrations below 1% are also effective. This advantage brings with it the favorable economical aspects of the process, when compared with the costly preparation of solutions with concentrations greater than 70% known from the prior art, as well as eliminating the necessity of maintaining said high concentration during the course of the process, while satisfying the security requirements already mentioned.

In an illustrative practical embodiment of the process, it is conducted as follows:

Into a reactor fitted with a stirrer, a heat-controlling system and a reflux coolant, there are introduced in preestablished quantities and ratios, the reactants ($H_2O_2$ and the olefin in the solvent). Thereupon, the catalytic system and the rest of the solvent are introduced, with the "onium" salt in the desired quantities. Under vigorous stirring, the heterogeneous mixture is brought to the reaction temperature for the desired time. At the end, after separation of phases and cooling down, etc., the epoxide and the reactants are separated by means of conventional methods (e.g., distillation, etc.).

The process proves particularly convenient thanks to the mild and simple operating conditions.

More particularly, it allows to effectively operate using high olefin concentrations in a solvent medium, or also in the absence of an extraneous solvent, thereby realizing the corresponding technological and economical advantages.

In the known processes which do not describe the use of solvents and which are conducted in a homogeneous phase with concentrated $H_2O_2$, there are prescribed large excesses of the starting olefin, necessary for ensuring reasonable margins of operational safety. This circumstance is not relevant in the case of the present process, in which, on the contrary, the difficulty concerning an aspect as important as is that of safety, is overcome by means of the double-phase technique.

Still other advantages are the possibility of using hydrogen peroxide at a low concentration, which may easily and economically be bought on the market or may be readily prepared without involving operational security risks.

Lastly, the high yields and high selectivity that are obtainable together with the other advantages noted, ensure a considerable interest in the industrial application of the process.

The compounds obtained, epoxides of olefins, are chemical products of a considerable industrial importance. In fact, they represent products that find interesting applications in industry, also on a high qualitative scale, within a wide range of uses well known to the skilled in general.

As a matter of fact, besides as useful intermediates in organic synthesis, amongst the main uses there may be listed those in which they are employed as intermediates in the production of urethanes, in the industry of blown or foamed products, of glycols for lubricants, surfactants, esters for plasticizers, polyester resins, etc.

The following further enabling examples are given for illustrative and not limiting purposes.

Examples 4, 6, 18 and 19 are given for comparative purposes in order to compare results under conditions of the Prior Art.

The symbol w/v stands for weight/volume.

EXAMPLE 1

Into a four-necked flask, fitted with a stirrer, a thermometer and provided with a reflux-coolant, there were introduced 22.1 g of octene-1 (0.197 mol), 0.8 g of tricaprylmethylammonium chloride (0.002 mol), 40 ml of $H_2O$, 1.65 g of $Na_2WO_4.2H_2O$ (0.005 mol), 0.83 g of $NaH_2PO_4.H_2O$ (0.006 mol), 2 ml of a 14.7% by w/v (0.003 mol) of $H_3PO_4$, 10.96 g of a 38.2% $H_2O_2$ (0.123 mol), 16 cc of 1,2 dichloroethane. Thereupon the mixture was additioned with 1.30 cc of $H_2SO_4$ at 31.7% concentration, and, under vigorous stirring the mixture was rapidly brought up to 70° C. and maintained at that temperature for 45 minutes. At the end, into the reaction medium there were dosed off, by the iodometric method, 0.0023 mol of unreacted $H_2O_2$ and by gas-chromatography (GLC) 0.102 mol of epoxyoctane, which corresponded to a conversion of the $H_2O_2$ equal to 98.1% with a selectivity in epoxyoctane of 84.5%.

EXAMPLE 2

Into a four-necked flask, fitted with a stirrer and provided with a thermometer and reflux-coolant, there were introduced 35.61 g of octene-1 (0.318 mol), 60 ml of benzene, 1.2 g of dicetyldimethylammonium chloride (0.002 mol), 40 ml of water, 3.3 g of $Na_2WO_4.2H_2O$ (0.010 mol), 7.0 ml of $H_3PO_4$ at 14.7% by w/v (0.0105 mol) and 11.47 g of $H_2O_2$ at a 38.2% concentration (0.129 mol). This mixture was thereupon rapidly brought up to 70° C., under vigorous stirring, and was then maintained at that temperature for 2 hours. At the end of the reaction, from the reaction mass were dosed off, by the iodometric method, 0.0097 mol of unreacted $H_2O_2$, and by gas-chromatography 0.1014 mol of epoxyoctane, which corresponded to a conversion of hydrogen peroxide of 92.4%, with a selectivity for epoxyoctane of 86.4%.

EXAMPLE 3

Into a four-necked flask, fitted with a stirrer, a thermometer and a reflux-coolant, there were introduced 22.1 g of 1-octene (0.197 mol), 1.2 g of dicetyldimethylammonium chloride (0.002 mol), 40 ml of $H_2O$, 1.65 g of $Na_2WO_4.2H_2O$ (0.005 mol), 0.83 g of $NaH_2PO_4.H_2O$ (0.006 mol), 2 ml of $H_3PO_4$ at 14.7% w/v (0.003 mol and 10.96 g of $H_2O_2$ at 38.2% (0.123 mol). Thereupon there were added 0.95 ml of $H_2SO_4$ at 31.7% concentration and, under vigorous stirring, the mixture was brought rapidly up to 70° C. and was then maintained at that temperature for 45 minutes. At the end of the reaction, from the reaction mass, by the iodometric method, there were dosed off 0.006 mol of unreacted $H_2O_2$ and by liquid gas chromatography (LGC) 0.0936 mol of epoxyoctane, corresponding to a conversion of the $H_2O_2$ of 95%, with a selectivity in epoxyoctane of 80%.

EXAMPLE 4 (COMPARATIVE EXAMPLE)

Example 2 was repeated, except that the $H_3PO_4$ was substituted with an equivalent quantity of $H_2SO_4$. After 2 hours of reaction, from the reaction product were dosed off 0.0986 mol of unreacted hydrogen peroxide and 0.007 mol of epoxyoctane, which corresponded to a conversion of hydrogen peroxide of 23.5%, with a selectivity in epoxyoctane of 23.2%.

EXAMPLE 5

Into a four-necked flask, fitted with a stirrer, a thermometer and a reflux-coolant, there were introduced 22.1 g of 1-octene (0.197 mol), 0.8 g (0.002 mol) of tricaprylmethylammonium chloride, 40 ml of $H_2O$, 1.65 g of $Na_2WO_4.2H_2O$ (0.005 mol), 3.12 g (0.010 mol) of $Na_2HAsO_4.7H_2O$, 10.96 g (0.123 mol) of a 38.2% $H_2O_2$ and 16 ml of 1,2-dichloroethane.

Thereupon about 3 ml of a 31.7% $H_2SO_4$ were added and, under vigorous stirring, the mixture was rapidly brought up to 70° C. and maintained there for 45 minutes. At the end of the reaction, from the reaction mixture were dosed off 0.0047 mol of unreacted $H_2O_2$ (conversion 96.2%) and 0.0978 mol of epoxy-octane (selectivity 82.6%).

EXAMPLE 6 (COMPARATIVE EXAMPLE)

Proceeding as in Example 5, but in the complete absence of tungstates and using 2.40 ml of a 31.7% $H_2SO_4$, after 60 minutes of reaction, from the reaction mass there was dosed off a quantity of $H_2O_2$ equal to that introduced initially. The LGC did not reveal the presence of any epoxyoctane.

EXAMPLE 7

Operations were as in Example 1, but using 0.93 g of hexadecyltributylphosphonium chloride (0.002 mol) instead of the quaternary ammonium salt. After 60 minutes of reaction, from the reaction mass there were dosed off 0.0051 mol of unreacted $H_2O_2$ (conversion=95.9%) and 0.0892 mol of epoxy-octane (selectivity=75.6).

EXAMPLE 8

Example 2 was repeated, using as a catalyst 2.46 g of sodium phosphotungstate (0.010 g-atom of W) and by adding to the reaction system 1.9 ml of NaOH at a 35% concentration. After 2 hours of reaction, as in Example 1, from the reaction product were dosed off 0.0376 mol of unreacted hydrogen peroxide and 0.0568 mol of epoxyoctane, which corresponded to a conversion of the hydrogen peroxide of 70.8%, with a selectivity for epoxyoctane of 62.1%.

EXAMPLE 9

Into a four-necked flask, fitted with a stirrer, a thermometer and a reflux-coolant, there were introduced 31.1 g (0.379 mol) of cyclohexene, 0.6 g (0.001 mol) of dicetyldimethylammonium chloride, 40 ml of $H_2O$, 0.66 g (0.002 mol) of $Na_2WO_4.2H_2O$, 1.1 ml (0.0015 mol) of a 14.7% $H_3PO_4$, 10.96 g (0.123 mol) of 38.2% $H_2O_2$ and 40 cc of benzene.

The mixture, subjected to vigorous stirring, was rapidly brought up to 70° C. and maintained at that temperature for 15 minutes. At the end of this period, from the reaction mixture there were dosed off 0.009 mol of unreacted $H_2O_2$ and 0.096 mol of epoxycyclohexane, which corresponded to a conversion of the hydrogen peroxide of 92.6%, with a selectivity in epoxycyclohexane of 84%.

EXAMPLE 10

Into a four-necked flask, fitted with a stirrer, a thermometer and a reflux-coolant, there were introduced 16.2 g of cyclohexene (0.197 mol), 60 ml of benzene, 1.2 g of dicetyldimethylammonium chloride (0.002 mol), 40 ml of water, 3.3 g (0.010 mol) of $Na_2WO_4.2H_2O$, 4.62 ml (0.0069 mol) of $H_3PO_4$ at 14.7% w/v and 11.47 g (0.129 mol) of $H_2O_2$ at 38.2% concentration.

This mixture was rapidly brought up to 70° C., under vigorous stirring, and was then maintained at that temperature for 30 minutes.

At the end of the reaction, from the reaction product were dosed off 0.015 mol of unreacted $H_2O_2$ and 0.099 mol of epoxycyclohexane, which corresponded to a conversion of the hydrogen peroxide of 88.4% with a selectivity in epoxycyclohexane of 86.8%.

EXAMPLE 11

Into a four-necked flask, fitted with a stirrer, a thermometer and a reflux-coolant, there were introduced 30.2 g (0.368 mol) of cyclohexene, 0.6 g (0.001 mol) of dicetyldimethylammoniumchloride, 40 cc of $H_2O$, 0.66 g (0.002 mol) of $Na_2WO_4.2H_2O$, 1.1 ml of a 14.7% w/v $H_3PO_4$ (0.0015 mol), and 11.2 g (0.126 mol) of a 38.2% $H_2O_2$.

Under vigorous stirring, the mixture was then brought up to 70° C. and maintained at that temperature for 15 minutes (initially the reaction was exothermic). At the end, from the reaction mixture were dosed off 0.0057 mol of unreacted $H_2O_2$ (conversion=95.5%) and 0.0985 mol of epoxycyclohexane (selectivity: 81.9% on $H_2O_2$).

EXAMPLE 12

Into a four-necked flask, fitted with a stirrer, a thermometer and a reflux-coolant, there were introduced 29.1 g (0.355 mol) of cyclohexene, 20 ml of 1,2-dichloroethane, 0.4 g (0.001 mol) of tricaprylmethylammonium chloride, 40 ml of water, 0.66 g (0.002 mol) of $Na_2WO_4.2H_2O$, 1.1 ml (0.0015 mol) of a 14.7% w/v $H_3PO_4$ and 10.96 g (0.123 mol) of a 38.2% $H_2O_2$.

The reaction mixture was then rapidly brought up to 70° C. and maintained at that temperature for 45 minutes. At the end of this period, from the reaction medium were dosed off 0.004 mol of unreacted $H_2O_2$ and 0.099 mol of epoxycyclohexane, which corresponded to a conversion of the hydrogen peroxide of 96.7%, with a selectivity in epoxycyclohexane of 83%.

EXAMPLE 13

Example 10 was repeated, using 4.9 ml of $H_3PO_4$ at 14.7% w/v (0.0074 mol) and operating at 50° C. After a reaction of 30 minutes, from the reaction mass there were dosed off 0.037 mol of unreacted $H_2O_2$ and 0.0848 mol of epoxycyclohexane, which corresponded to a conversion of the hydrogen peroxide of 71.3%, with a selectivity for epoxycyclohexane of 92.1%.

EXAMPLE 14

Example 13 was repeated, bringing the reaction time to 1 hour. From the reaction product were then dosed off 0.0122 mol of unreacted hydrogen peroxide and 0.0951 mol of epoxycyclohexane, which corresponded to a conversion of the hydrogen peroxide of 90.5%, with a selectivity in epoxycyclohexane equal to 81.4%.

EXAMPLE 15

Example 10 was repeated, using 3.96 g of $WCl_6$ (0.010 mol instead of $Na_2WO_4.2H_2O$ and 3.58 g (0.010 mol) of $Na_2HPO_4.12H_2O$ instead of $H_3PO_4$. To this reaction mass were then additioned 8.5 ml of a 35% NaOH. After 30 minutes of reaction there were then dosed off 0.01057 mol of unreacted hydrogen peroxide and 0.0688 mol of epoxycyclohexane, which corresponded to a conversion of hydrogen peroxide of 91.6%, with a selectivity for epoxycyclohexane of 55.9%.

EXAMPLE 16

Example 10 was repeated, but using 3.52 g of $W(CO)_6$ (0.010 mol) instead of $Na_2WO_4.2H_2O$ and 3.58 g (0.010 mol) of $Na_2HPO_4.12H_2O$ instead of $H_3PO_4$. To this mixture were then added 2 ml of $H_2SO_4$ at a concentration of 31.7%. After 30 minutes of reaction, there were dosed off 0.00506 mol of unreacted hydrogen peroxide and 0.0565 mol of epoxycyclohexane, which corresponded to a conversion of the hydrogen peroxide of 96.1%, with a selectivity for epoxycyclohexane of 43.6%.

EXAMPLE 17

Example 10 was repeated, using however 4.4 ml of $H_3PO_4$ at a 14.7% w/v concentration, (0.0066 mol), operating at a temperature of 50° C. and by prolonging the reaction time to 1 hour. Thereupon, there were dosed off 0.0407 mol of unreacted hydrogen peroxide and 0.0805 mol of epoxycyclohexane, which corresponded to a conversion of the hydrogen peroxide of 68.4%, with a selectivity for the epoxycyclohexane of 91.1%.

EXAMPLE 18 (COMPARATIVE EXAMPLE)

The procedure was as in Example 17, but substituting the phosphoric acid with an equivalent quantity of $H_2SO_4$. After 30 minutes of reaction, from the reaction mass there were dosed off 0.00413 mol of epoxycyclohexane.

EXAMPLE 19 (COMPARATIVE EXAMPLE)

Operations were as in Example 17, but in the absence of $Na_2WO_4.2H_2O$ and by substituting $H_3PO_4$ with 0.9 g (0.006 mols) of $NaH_2PO_4.H_2O$. After 30 minutes of reaction, the hydrogen peroxide was found to have remained unaltered and no presence of epoxycyclohexane was detected by LGC.

EXAMPLE 20

Example 13 was repeated, but using 2.42 g (0.010 mol) of $Na_2MoO_4.2H_2O$ instead of $Na_2WO_4.2H_2O$, and 5.1 g (0.0077 mol) of $H_3PO_4$ at 14.7% w/v.

After 30 minutes of reaction, from: the reaction mass there were dosed off 0.1088 mol of unreacted hydrogen peroxide and 0.0010 mol of epoxycyclohexane, which corresponded to a conversion of the hydrogen peroxide of 15.6% with a selectivity for the epoxycyclohexane of 49.5%.

EXAMPLE 21

Example 10 was repeated, but using, instead of $Na_2WO_4.2H_2O$ and $H_3PO_4$, 2.46 g of $2Na_3PO_4.24WO_3.H_2O$ (sodium phosphotungstate) equal to 0.010 g-atom of W and to 0.0008 g-atom of P. To this mixture were then added 1.9 ml of a 35% NaOH.

After 30 minutes of reaction, from the reaction mass were dosed off 0.0877 mol of unreacted hydrogen peroxide and 0.0245 mol of epoxycyclohexane, which corresponded to a conversion of the hydrogen peroxide of 32.1%, with a selectivity for the epoxycyclohexane of 59.3%.

EXAMPLE 22

Example 2 was repeated but using 2.42 g (0.010 mol) of $Na_2MoO_4.2H_2O$ instead of $Na_2WO_4.2H_2O$ and using 1,2-dichloroethane (60 ml) instead of benzene as a solvent.

After 2 hours of reaction, from the reaction product were dosed off, iodometrically, 0.1105 mol of unreacted hydrogen peroxide and 0.0081 mol of epoxyoctane, which corresponded to a conversion of the hydrogen peroxide of 14.3%, with a selectivity for the epoxyoctane of 43.8%.

EXAMPLE 23

Example 1 was repeated, but substituting the 1-octene with 33.35 g (0.1985 mol) 1 dodecene. After 1 hour, from the reaction product were dosed off 0.0059 mol of hydrogen peroxide and 0.0958 mol of 1,2-epoxydodecane, which corresponded to a conversion of the hydrogen peroxide of 91.9%, with a selectivity for the epoxydodecane of 80.7%.

EXAMPLE 24

Into an autoclave of 1 liter holding capacity, lined with glass and provided with a magnetic stirrer, there were introduced 2.48 g (0.0075 mol) of $Na_2WO_4.2H_2O$, 1.25 g (0.009 mol) of $NaH_2PO_4.H_2O$, 2.9 ml (0.0044 mol) of $H_3PO_4$ at 14.7% w/v, 0.25 ml of $H_2SO_4$ at 31.7% concentration, 50 ml of 1,2 dichloroethane, 1.3 g (0.0032 mol) of tricapryl-methylammonium chloride, 32.35 g (0.363 mol) of $H_2O_2$ at 38.2% concentration.

After removal of the air from the autoclave, 72 g of propylene (1.714 mol) were loaded into the autoclave. The reaction mass was thereupon heated up to 60° C. under vigorous stirring, thereby attaining a pressure of 18 atmospheres. The reaction mixture was then maintained at this temperature for 1 hour. At the end of this period, after cooling down, there were dosed off 6.32 g (0.186 mol) of unreacted $H_2O_2$ and 6.73 g (0.116 mol) of propylene oxide, which corresponded to a converstion of the hydrogen peroxide of 48.76%, with a selectivity for the propylene oxide of 65.5%. Moreover 0.63 g (0.008 mol) of propylene glycol was also obtained.

What is claimed is:

1. A process for the expoxidation of aliphatic olefins wherein said olefins have the formula:

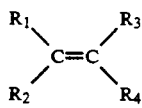

wherein $R_1$, $R_2$, $R_3$, and $R_4$ are the same or different and are selected from the group consisting of a hydrogen atom, alkyl having up to 30 carbon atoms, and alkenyl having up to 30 carbon atoms comprising reacting said aliphatic olefin with hydrogen peroxide, according to the double phase technique and using quaternary salts, in an aqueous-organic two-phase liquid system consisting essentially of the olefin as the organic phase and of an aqueous acid phase containing the hydrogen peroxide, wherein the expoxidation is carried out at 0°-120° C., at 1-100 atmospheres, and at a pH from 1.82 to 3.60, in the presence of a catalytically active system consisting essentially of two components, the first component comprising a tungsten atom W and being selected from the group consisting of metallic tungsten; tungstic mixed oxides; tungstic oxyacids and salts thereof; isopoly-tungstic acids and salts thereof; heteropolytungstic acids and salts thereof; tungsten sulphides and other tungsten salts derived from hydrogen acids; tungsten naphthenates; tungsten acetylacetonates and other carbonylic compounds containing tungsten;

and the second component being selected from the group consisting of phosphorus oxides; phosphorus oxyacids and salts thereof; phosphorus sulphides and other phosphorus salts derived from hydrogen acids; and phosphorus compounds having the formula:

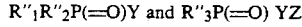

wherein $R''_1$, $R''_2$ and $R''_3$ are selected from the group consisting of a hydrogen atom, alkyl, cycloalkyl, aryl or aryl-alkyl having up to 12 carbon atoms, and Y and Z are selected from the group consisting of H, alkyl, aryl, aralkyl and hydroxy groups, halogens, alkoxy groups, carboxyl groups and groups coming from mineral oxyacids;

said quaternary salts having the formula:

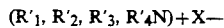

wherein X is an anion selected from the group consisting of Cl—, Br—, HSO—$_4$, and NO—$_3$, and $R'_1$, $R'_2$, $R'_3$, $R'_4$, which may be the same or different, represent hydrocarbyl groups having an overall number of C atoms up to 70, and a mutual W:P molar ratio ranging from 1.5 to 0.25.

2. The process of claim 1, wherein the olefin is substituted with a group selected from hydroxyl, halogen, nitro, alkoxyl, amine, carbonyl, carboxyl, ester, amide and nitrile groups.

3. The process of claim 1, wherein $R'_1$, $R'_2$, $R'_3$ and $R'_4$ represent hydrocarbyl groups having a total number of C atoms from 25 to 40.

4. The process of claim 1, wherein said first component is selected from W in the metal state, tungstic acid and the corresponding neutral salts or acids of an alkali metal or alkaline earth metal, the metal-carbonyl $W(CO)_6$; the oxides: $WO_2$, $W_2O_5$, $WO_3$, $WS_2$ and $WS_3$ sulphides and oxychlorides, chlorides, naphthenates and stearates of tungsten.

5. The process of claim 1, wherein said second component consists of at least one mineral, organic or organo-metallic derivative of phosphorus, which forms, under reaction conditions, the catalytically active system with the first catalyst component.

6. The process of claim 5, wherein the second component is selected from phosphorous, phosphoric, polyphosphoric, pyrophoshoric, phosphonic acids and their alkali metal salts; the oxides: $P_2O_3$ and $P_2O_5$; and oxychlorides, fluorides and chlorides of phosphorus.

7. The process of claim 1, wherein the amount of tungsten is from 0.0001 to 1 mole per mole of hydrogen peroxide.

8. The process of claim 7, wherein said amount is from 0.005 to 0.2 mole per mole of $H_2O_2$.

9. The process of claim 1, wherein the amount of quaternary salt is from 0.01 to 2 moles per mole of tungsten.

10. The process of claim 9, wherein said amount is from 0.1 to 1.0 mole per mole of tungsten.

11. The process of claim 1, wherein the quaternary salt is selected from dicetyldimethylammonium chloride, tricapryl-ammonium chloride and hexadecyltributylphosphonium chloride.

12. The process of claim 1, wherein the olefin:$H_2O_2$ ratio is from 0.1 to 50 by moles.

13. The process of claim 12, wherein the olefin:$H_2O_2$ ratio is from 1 to 20 by moles.

14. The process of claim 1, wherein the olefin concentration in the organic phase is from 5% to 95% by weight.

15. The process of claim 1, wherein the hydrogen peroxide concentration in the aqueous phase is from 0.1% to 70% by weight.

16. The process of claim 15, wherein said hydrogen peroxide concentration is from 1% to 10%.

17. The process of claim 1, wherein the solvent for the organic phase, substantially inert and immiscible with the aqueous phase, is selected from aliphatic, alicyclic and aromatic hydrocarbons, chlorinated hydrocarbons, alkyl esters and mixtures thereof.

18. The process of claim 17, wherein the solvent is selected from benzene and 1,2-dichloroethane.

19. The process of claim 1, wherein said alkenyl is selected from dienes and trienes, conjugated or not.

20. The process of claim 1, wherein said aliphatic olefin is a linear or branched mono- or di-olefin having up to 20 carbon atoms.

21. The process of claim 20, wherein said aliphatic olefin is selected from propylene, butene and pentene.

22. The process of claim 12, wherein the olefin:$H_2O_2$ ratio is substantially equimolar.

23. The process of claim 15, wherein the hydrogen peroxide concentration is from 0.1 to 10%.

24. The process of claim 1, wherein the organic phase comprises said aliphatic olefin in the absence of solvent.

25. The process of claim 1, wherein said epoxidization reaction occurs over a time in the range from 15 minutes to two hours.

26. The process of claim 25, wherein said epoxidation reaction temperature is in the range from 50° to 70° C.

* * * * *